US006491952B1

(12) United States Patent
Sjoberg

(10) Patent No.: US 6,491,952 B1
(45) Date of Patent: Dec. 10, 2002

(54) CHOLESTEROL LOWERING COMPOSITION

(75) Inventor: Kjell Sjoberg, Danderyd (SE)

(73) Assignee: Triple Crown AB, Stockholm (SE)

( * ) Notice: Subject to any disclaimer, the term of this patent is extended or adjusted under 35 U.S.C. 154(b) by 0 days.

(21) Appl. No.: 09/509,281

(22) PCT Filed: Apr. 30, 1999

(86) PCT No.: PCT/SE99/00721

§ 371 (c)(1),
(2), (4) Date: Mar. 22, 2000

(87) PCT Pub. No.: WO99/56729

PCT Pub. Date: Nov. 11, 1999

(30) Foreign Application Priority Data

Apr. 30, 1998 (SE) ................................................ 9801536

(51) Int. Cl.[7] ........................ A61K 31/575; A61K 9/10; A61K 9/22; A61K 9/52; A61K 9/12
(52) U.S. Cl. ........................ 424/488; 424/439; 424/484; 424/487; 424/457; 424/468; 424/400; 512/182; 512/170
(58) Field of Search ................... 514/170, 182; 424/439, 484, 487, 488, 457, 468, 400

(56) References Cited

U.S. PATENT DOCUMENTS

| 3,881,005 A | 4/1975 | Thakkar et al. ............. 424/238 |
| 5,244,887 A | 9/1993 | Straub ........................ 514/182 |

FOREIGN PATENT DOCUMENTS

| DE | 4038385 | 6/1992 |
| EP | 0357967 | 3/1990 |
| GB | 1365661 | 9/1974 |

OTHER PUBLICATIONS

Nisshin Oil Mills Ltd., "Instant powder compsns with improved dispersibility—contg. lecithin and sterol (deriv.)", File WPI, Derwent accession No. 87–196297.

Primary Examiner—Edward J. Webman
Assistant Examiner—Helen Nguyen
(74) Attorney, Agent, or Firm—Birch, Stewart, Kolasch & Birch, LLP

(57) ABSTRACT

The present invention concerns a composition containing a cholesterol lowering component such as β-sitosterol and/or β-sitostanol in a monomolecular, low associated or "cluster" form, where a melt and/or solution of the said components are distributed, immobilised and stabilised in a matrix; food containing such a composition and a method of preparing this composition.

21 Claims, No Drawings

CHOLESTEROL LOWERING COMPOSITION

TECHNICAL FIELD

The present application describes a composition containing a cholesterol lowering component, as β-sitosterol and/or β-sitostanol, food containing such a composition, and a method to prepare the composition.

BACKGROUND OF THE INVENTION

A daily intake of some compounds similar to cholesterol has been shown to have a cholesterol lowering effect. Specifically this is true for β-sitosterol and the hydrogenated form β-sitostanol (1–5).

Under β-sitosterol is also understood mixtures containing β-sitosterol, β-sitostanol and campesterol isolated from for instance soy or tall oil. Under β-sitostanol is also understood fully or partly hydrogenated β-sitosterol as above.

It is known that sterols and stanols are compounds with a very low solubility. They also crystallize easily. Several researchers have pointed at the importance that β-sitosterol and β-sitostanol must be administered in a formulation giving the optimal cholesterol lowering effect in the body. In a crystalline form even after efficient micronisation and/or in suspension the effect is lower than for solutions or emulsions (6–15). Hitherto described solutions and emulsions, however, have the disadvantage being too dilute to allow a simple intake in doses necessary of about 1.5 g/day (16–18).

The solubility in fat of sterols and stanols, both being alcohols, can be increased considerably by esterification with fatty acids. These esters are hydrolyzed in the stomach and sterols and stanols are liberated as the initial alcohols in a concentration low enough not to allow re-crystallization. The cholesterol lowering effect in the gut is thus improved (16–20).

We have now shown that it is not necessary to esterify sterols and stanols to be able to distribute them in a sufficiently high concentration in a monomolecular, low associated or "cluster form" to reach necessary daily doses.

DESCRIPTION OF THE INVENTION

In the present invention we show how sterols and stanols by simple methods can be stabilised in monomolecular, low associated or "cluster" form by distributing and immobilising a solution of high concentration or a melt of sterols and/or stanols in a matrix.

Sterols and/or stanols are initially dissolved in an organic phase, for instance in mono, di- or triglycerides, fatty acids, lecithin and others preferentially at an elevated temperature. The solution is then mixed with a stabilising phase matrix, containing a high molecular material e.g., gelatin, casein, starch syrup, pectin, ethylhydroxyethylcellulose or other at an elevated temperature. The mixture is then allowed to set to a solid, rubberlike or highly viscous mass. The stabilising phase can also be based on solvents being solid at room temperature.

An alternative way to make the composition is to foam a solution of the sterols and/or stanols containing a solvent solid at room temperature possibly in the presence of a foam building component under rapid cooling. The surface of sterols and/or stanols accessible to the stomach thus becomes extremely large. Foaming can be done in different known ways. Some percent of ethanol can be added to the sterols and/or stanols, the mixture is melted at elevated temperatures, the alcohol evaporated in vacuo under formation of foam.

The solutions described above can also be mixed into different food e.g. chocolate, dough/bread, jelly, mashed potatoes, butter/margarine, yougurt and others or be encapsulated or mixed into tablets.

The special characteristics of the present innovation are also shown by the enclosed claims.

The present innovation is described below by not limiting examples. If not otherwise stated the given values are in weight or weight %.

EXAMPLE 1

30 g of β-sitostanol were dissolved in 70 g of a monoglyceride such as Dimodan RT oil at 90° C. on a hot water bath and stirred until the stanol was completely dissolved. The 30% solution can be used directly or stored as a prefabricate after cooling as a homogenous mass. 20 g of the solution obtained were slowly added under intensive stirring to 80 g of a 35% solution of gelatin and agar 10:1, starch syrup, sugar and aroma in water placed on a hot water bath at 65° C. The liquid highly viscous composition was immediately cast in small forms, where it solidified as a gel containing β-sitostanol in a stabilised monomolecular or low associated form. The composition can be used as such or be mixed into food and/or be foamed, encapsulated or made into tablets.

EXAMPLE 2

10 g of β-sitostanol were dissolved in 10 g of Dimodan RT at 120° C. on an oil bath. The solution was carefully under intensives stirring added to 80 g of a 30% solution of gelatin in water, also containing sugar and aroma, placed on a water bath of 85° C. The homogenous stabilised composition was then treated as in example 1.

EXAMPLE 3

10 g of β-sitosterol were dissolved in 10 g of rapeseed oil at 120° C. on an oil bath. The solution was carefully under intensive continous stirring added to 30 g of a 30% solution of gelatin in water, containing sugar and aroma, placed on a hot water bath of 95° C. The homogenous stabilised composition was then treated as in example 1.

EXAMPLE 4

10 g of β-sitostanol were dissolved in 10 g of rapeseed oil at 130° C. on an oil bath. The solution was carefully added under intensive continous stirring to 50 g of a 30% solution of gelatin in water, containing sugar and aroma, placed on a hot oil bath of 110° C. The homogenized stabilized composition was then treated as in example 1.

EXAMPLE 5

10 g of β-sitostanol were dissolved in 10 g of Dimodan RT at 120° C. on an oil bath. In another flask 80 g, of chocolate mass were melted on the same bath. The 50% solution of β-sitostanol was slowly added under continous stirring to the chocolate. The composition was directly cast in forms, where it solidified and could be used as such or mixed into food or tableted, encapsulated or foamed.

EXAMPLE 6

10 g of β-sitostanol were dissolved in 10 g of rapeseed oil at 130° C. on an oil bath. In another flask 40 g of chocolate mass were melted at 110° C. on an oil bath. The 50% solution of β-sitostanol was added under continous stirring to the chocolate. The composition was directly cast in forms where it solidified and can be used as such or mixed into food or be tableted, encapsulated or foamed.

EXAMPLE 7

30 g of β-sitostanol were dissolved in 30 g stearic acid at 130° C. on an oil bath. A few drops of ethanol were added under intensive stirring and the composition was placed under vacuum. The mass bubbled up and was allowed to solidify as a foamed material that could be mixed in, for instance, flour, dough, mashed potatoes or other food material, encapsulated or tableted. Alternatively the composition can be directly cooled and used as such, mixed into food, encapsulated or tableted.

EXAMPLE 8

2.5 g of β-sitosterol were dissolved in 2.5 g of 2.5 g of Dimodan ML at 80° C. The solution was added to 1 liter of a 3% solution of sodium caseinate at 60–80° C. under strong stirring with a Turrax. After 5 minutes the emulsion was cooled to 20° C. and can be used as a beverage. The emulsion can be kept in a fridge during at least 3 days. The same result is obtained using milk.

EXAMPLE 9

12.5 g of β-sitosterol were dissolved in 25 g 2.5 g of Dimodan ML at 60° C. The solution was added to 80 g of melted margarine and mixed with 125 g of flour, 175 g of oat flakes, 2.5 g of baking powder and 80 g of sugar to a dough. The mixture was baked into 25 cakes of 18–20 g each containing 0.5 g of β-sitosterol.

REFERENCES

1 Pollak, O. J., Reduction of blood cholesterol in man. Cirkulation, 7, 702–706, (1953)
2 Grundy, S. M., Ahrens, E. H. Jr., and Davignon, J., The interaction of cholesterol absorption and cholesterol synthesis in man. J. Lipid Res., 10,304,(1969).
3 Farguhar, J. W. and Sokolow, M., Response of serum lipids and lipoproteins of man to beta-sitosterol and sanflower oil—A long term study, Cirkulation, 17, 890,(1956).
4 Oster, P., Schlierf, G., Heuck, C. C., Greten, H., Gundert-Remy, U., Haase, W. Klose, G., Nothelfer, A., Raetzer, H., Schellenberg, B. und Schmidt-Gauk, H., Sitosterin bei fam familiären Hyperlipoproteinämmie Tyo II. Eine randomisierte gekreuzte Doppelblindstudie, Dtsch. Med. Wschr., 101, 1308–1311, (1976).
5 Grundy, S. M., Mok, H. Y. I., Effekts of low dose phytosterols on cholesterol absorption in man, "Lipoprotein metabolism"., p114–118, Ed greten, H., Berlin, Heidelberg, New York, Springer-Verlag, (1976).
6 Miettinen, T. A., Siurala, M., Bile salts, sterols, sterol esters glycerides and fatty acids in micellar and oil phases of inerstinal contents during fat digestion in man, Z. Klin. Chem. Biochem., 9, 47–52, (1979).
7 Kudchodkar, B. J., Horlick, L., Sodhi, H, S. Effekts of plant sterols on cholesterol metabolism in man, Atherosclerosis, 23, 239, (1976).
8 Hassan, A. s., Rampone, A. J., Intestinal absorption and lymphatic transport of cholesterol and β-sitostanol in the rat, J. Lipid Res., 20, 646–653, (1979).
9 Heinemann, T., Kullak-Ublick, G.-K., Pietruck, B., von Bergman, K., Mechanisms of action of plants sterols on inhibition of cholesterol absorption, Eur. J. Clin. Pharmacol., 40 Suppl., 50–63, (1991).
10 Ikeda, I., Tanaka, K., Sugano, M., Vahouny, G. V., Gallo, I L., Inhibition of cholesterol absorption in rats by plant sterols, J. Lipid Res., 29, 1573–1582, (1988).
11 Ikeda, I., Tanaka, K., Sugano, M., Vahouny, G. V., Gallo, I L., Discrimination between cholesterol and sitosterol for absorption in rats, J. Lipid Res., 29, 1583–1592, (1988).
12 Ikeda, I., Tanabe, Y and Sugano, M., Effects of sitosterol and sitostanol on micellar solubility of cholesterol, J. Nutr. Sci. Vitaminol., 35, 361–369, (1989).
13 Ikeda, I., Sugano, M., Comparison of absorption and metabolism of beta-sitosterol in rats, Atherosclerosis, 30, 227, (1978).
14 Sugano, M., Marioka, H. and Ikeda, I., A comparison of hypocholesterolemic activity of β-sitosterol and β-sitostanol in rats, J., Nutr., 107, 2011–2019, (1977).
15 Heinemann, T., Pietruck, B., Kullak-Ublick, G.-K., Pietruck, B., von Bergman, K., Comparison of sitosterol and sitostanol on inhibition of intestinal cholesterol absorption, Agents Action (Suppl) 26, 117–122, (1988).
16 Heinemann, T., Leiss, O., B., von Bergman, K., Effects of low-dose sitotanol on serum cholesterol in patients with hypercholesterolemia, Atherosclerosis, 61, 219–223, (1986).
17 Miettinen, T. A., Vanhanen, H., Dietary sitostanol related to absorption, synthesis and serum level of cholesterol in different apolipoprotein e-phenotypes, Atherosclerosis, 105, 217–226, (1994).
18 Mattson, F., H., Volpenstein, R., A., Erickson, B., A., Effects of plant sterol esters on the absorption of dietary cholesterol, J. Nutr., 107, 1139–1146 (1977)
19 Mattson, F., H., Grundy, S. M., Crouse, J. R., Optimizing the effect of plant sterols on cholesterol absorption in man, Am. J. Clin. Nutr., 35, 697–700, (1982).
20 A substance for lowering high cholesterol level in serum and method for preparing the same. Patent C07J 9/00, A61K31/575.

What is claimed is:

1. A composition, comprising:
   (1) a solid or viscous matrix; and
   (2) at least one cholesterol lowering agent selected from the group consisting of β-sitosterol and β-sitostanol, wherein,
      (a) said cholesterol lowering agent is dissolved in an organic phase,
      (b) said cholesterol lowering agent in said organic phase is distributed within said matrix, and
      (c) said cholesterol lowering agent dissolved in the organic phase is stable within said matrix.

2. The composition according to claim 1, said matrix comprising at least one material selected from the group consisting of gelatin, casein, stearic acid, chocolate mass and dough.

3. The composition according to claim 2, said matrix further comprising at least one material selected from the group consisting of pectin, agar, ethylhydroxyethyl cellulose, starch and starch syrup.

4. The composition according to claim 1, wherein said organic phase contains said cholesterol lowering agent and at least one material selected from the group consisting of monoglycerides, diglycerides, triglycerides, fatty acids and lecithin.

5. The composition according to claim 1, wherein said cholesterol lowering agent is β-sitosterol.

6. The composition according to claim 1, wherein said cholesterol lowering agent is β-sitostanol.

7. The composition according to claim 4, wherein said organic phase contains said cholesterol lowering agent and monoglycerides of partially-hydrogenated rapeseed oil.

8. The composition according to claim 4, wherein said matrix is based on a 10–50% solution of gelatin in water.

9. The composition according to claim 4, wherein the matrix comprises stearic acid and a foam building agent.

10. The composition according to claim 4, wherein said cholesterol lowering agent is present in amounts of from 1–99% of the organic phase.

11. The composition according to claim 10, wherein said organic phase contains said cholesterol lowering agent and a monoglyceride.

12. The composition according to claim 4, wherein said cholesterol lowering agent is present in amounts of 30–50% of the organic phase.

13. The composition according to claim 4, wherein said composition is in the form of a foam.

14. A capsule, tablet or foam containing the composition, according to claim 1.

15. A food product comprising:

a foodstuff; and an effective cholesterol lowering amount of the composition according to claim 1.

16. The food product-according to claim 15, wherein said foodstuff is selected from the group consisting of butter, butter substitute, margarine, chocolate, jelly, bread, mashed potatoes, yogurt, beverage, and soup.

17. The food product according to claim 15, wherein the cholesterol lowering agent is present in an amount of up to 60% of the food.

18. A method manufacturing a cholesterol lowering composition comprising:

melting or dissolving a cholesterol lowering agent selected from the group consisting of β-sitosterol and β-sitostanol, in a heated organic phase to obtain a melt or solution containing the cholesterol lowering agent;

distributing said melt or solution containing the cholesterol lowering agent in said matrix, wherein the cholesterol lowering agent dissolved in the organic phase is stable within said matrix.

19. The method according to claimed 18, further comprising cooling the distributed cholesterol lowering agent within the matrix, prior to final stabilization.

20. The method according to claim 18, further comprising foaming the distributed cholesterol lowering agent within the matrix, prior to stabilization.

21. The method according to claim 18, wherein said organic phase is solid at room temperature.

* * * * *

UNITED STATES PATENT AND TRADEMARK OFFICE
Certificate

Patent No. 6,491,952 B1                                                              Patented: December 10, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kjell Sjoberg, Danderyd, Sweden; and Sergej Bolkhovets, Taby, Sweden.

Signed and Sealed this Seventh Day of October 2003.

S. PADMANABHAN
*Supervisory Patent Examiner*
Art Unit 1617